US011660389B2

(12) United States Patent
Barnes et al.

(10) Patent No.: US 11,660,389 B2
(45) Date of Patent: May 30, 2023

(54) SEMI-RIGID AND FLEXIBLE ELEMENTS FOR WEARABLE DRUG DELIVERY DEVICE RESERVOIR

(71) Applicant: Insulet Corporation, Acton, MA (US)

(72) Inventors: Jeff Barnes, Medford, MA (US); Jackie Mac, Malden, MA (US); Ian McLaughlin, Groton, MA (US); David Nazzaro, Groveland, MA (US); Steven Cardinali, Woburn, MA (US); Thomas Metzmaker, Harvard, MA (US)

(73) Assignee: INSULET CORPORATION, Acton, MA (US)

( * ) Notice: Subject to any disclaimer, the term of this patent is extended or adjusted under 35 U.S.C. 154(b) by 231 days.

(21) Appl. No.: 16/514,621

(22) Filed: Jul. 17, 2019

(65) Prior Publication Data

US 2020/0023119 A1    Jan. 23, 2020

Related U.S. Application Data

(60) Provisional application No. 62/772,551, filed on Nov. 28, 2018, provisional application No. 62/736,172, (Continued)

(51) Int. Cl.
*A61M 5/148* (2006.01)
*A61J 1/20* (2006.01)
*A61M 5/142* (2006.01)

(52) U.S. Cl.
CPC ............ *A61M 5/148* (2013.01); *A61J 1/2024* (2015.05); *A61M 5/14248* (2013.01); *A61M 2205/3334* (2013.01); *A61M 2205/3379* (2013.01)

(58) Field of Classification Search
CPC .. A61M 5/145; A61M 5/14586; A61M 5/148; A61M 5/152
See application file for complete search history.

(56) References Cited

U.S. PATENT DOCUMENTS 3,926,341 A * 12/1975 Lhoest ...................... A61J 1/05
  222/105
4,991,743 A    2/1991 Walker
(Continued)

FOREIGN PATENT DOCUMENTS

CN    107096091 A    8/2017
EP    0789146 A1    8/1997
(Continued)

OTHER PUBLICATIONS

Merriam-Webster defintion of 'shell', https://www.merriam-webster.com/dictionary/shell, last visited Sep. 20, 2022. (Year: 2022).*
(Continued)

*Primary Examiner* — Laura A Bouchelle
(74) *Attorney, Agent, or Firm* — Goodwin Procter LLP

(57) ABSTRACT

Disclosed are examples of reservoir and reservoir systems usable with a wearable drug delivery device. An example reservoir may include a flexible component coupled to a shell component. The shell component may include drainage channels to facilitate extraction of the liquid drug from the reservoir. A reservoir system example may include an exoskeleton configured around a flexible reservoir to guide the expansion and collapse of the flexible reservoir. Alternatively, one or more rigid panels may be coupled to corresponding flat surfaces of the flexible reservoir to guide the expansion and collapse of the flexible reservoir. A further reservoir example may include a flexible thin film reservoir having peel-able restraints configured to seal off corresponding sections of the reservoir, sequentially break, enabling the liquid drug to sequentially fill corresponding sections in a
(Continued)

controlled and predicable manner. A wearable drug delivery device example suitable for utilizing the described examples is provided.

20 Claims, 9 Drawing Sheets

Related U.S. Application Data filed on Sep. 25, 2018, provisional application No. 62/699,023, filed on Jul. 17, 2018.

(56) References Cited

U.S. PATENT DOCUMENTS

| | | | |
|---|---|---|---|
| 5,368,570 A * | 11/1994 | Thompson | A61M 5/152 |
| | | | 604/185 |
| 5,693,018 A * | 12/1997 | Kriesel | A61M 5/14248 |
| | | | 604/890.1 |
| 5,906,592 A | 5/1999 | Kriesel et al. | |
| 6,086,561 A * | 7/2000 | Kriesel | A61M 5/152 |
| | | | 604/133 |
| 6,740,059 B2 | 5/2004 | Flaherty | |
| 7,137,964 B2 | 11/2006 | Flaherty | |
| 7,303,549 B2 | 12/2007 | Flaherty | |
| 8,734,396 B2 * | 5/2014 | Wyss | A61M 5/148 |
| | | | 604/151 |
| 9,579,461 B2 * | 2/2017 | Sonderegger | A61M 5/14586 |
| 9,907,904 B2 * | 3/2018 | Sage, Jr. | A61M 5/14248 |
| 2003/0198558 A1 | 10/2003 | Nason et al. | |
| 2004/0115068 A1 | 6/2004 | Hansen et al. | |
| 2007/0255260 A1 | 11/2007 | Haase | |
| 2011/0108158 A1 | 5/2011 | Huwiler et al. | |
| 2011/0319814 A1 | 12/2011 | Sullivan et al. | |
| 2013/0253439 A1 * | 9/2013 | Wyss | A61J 1/05 |
| | | | 604/246 |
| 2017/0290975 A1 | 10/2017 | Barmaimon et al. | |

FOREIGN PATENT DOCUMENTS

| | | |
|---|---|---|
| EP | 1065378 A2 | 1/2001 |
| EP | 2229970 A1 | 9/2010 |
| EP | 2556815 A1 | 2/2013 |
| WO | 2012065780 A2 | 5/2012 |
| WO | 2013149186 A1 | 10/2013 |

OTHER PUBLICATIONS

European Search Report and Written Opinion, Application No. EP02768908, dated Apr. 30, 2010, 6 pages.
International Search Report and Written Opinion, Application No. PCT/US2019/042233, dated Jan. 3, 2020, 17 pages.
International Search Report and Written Opinion, Application No. PCT/US2021/060148, dated Mar. 17, 2022, 17 pages.
International Search Report and Written Opinion, Application No. PCT/US2022/016713, dated Aug. 5, 2022, 19 pages.

* cited by examiner

SEMI-RIGID AND FLEXIBLE ELEMENTS FOR WEARABLE DRUG DELIVERY DEVICE RESERVOIR

CROSS-REFERENCE TO RELATED APPLICATIONS

This application claims priority to provisional application No. 62/699,023, entitled SEMI-RIGID AND FLEXIBLE ELEMENTS FOR WEARABLE DRUG DELIVERY DEVICE CONTAINER, filed on Jul. 17, 2018, the entire contents of which are incorporated herein by reference.

This application also claims priority to provisional application No. 62/736,172, entitled CONTROLLED EXPANSION AND COLLAPSE OF FLEXIBLE ELEMENTS FOR WEARABLE DRUG DELIVERY DEVICE CONTAINER, filed on Sep. 25, 2018, the entire contents of which are incorporated herein by reference.

This application further claims priority to provisional application No. 62/772,551, entitled HEAT STAKE PEELABLE FILL BARRIERS AND VAPOR TRANSMISSION BARRIERS, filed on Nov. 28, 2018, the entire contents of which are incorporated herein by reference.

TECHNICAL FIELD

The present application generally relates to medication delivery devices, and more particularly to reservoirs or reservoirs for storing a liquid drug within a drug delivery device.

BACKGROUND

Many conventional wearable drug delivery systems include either a fully rigid reservoir or a fully flexible reservoir for storing a liquid drug. Each type of reservoir includes one or more advantages and disadvantages over the other type of reservoir. Fully rigid reservoirs take up space that may be better used. While fully flexible reservoirs may be space efficient and may require relatively lower pumping pressures, the flexible reservoirs present challenges compared to fully rigid reservoirs. For example, the expansion and collapse of earlier flexible reservoirs may be unpredictable, thereby leading to undesirable hold up volumes and difficulties in determining stored fluid volumes (e.g., inaccurate fill gauging). Flexible reservoirs also present challenges related to vapor transmissivity. In some instances, a small volume of fluid is spread across a large surface area on a thin flexible membrane. This may lead to higher vapor transmission rates and may negatively impact medication concentration/potency.

SUMMARY

Disclosed is an example of a reservoir for storing a liquid drug. The reservoir includes a shell component, a flexible component and a port. The flexible component is coupled to the shell component. The coupling is a hermetic seal. The port is configured to enable filling or emptying of the reservoir.

An example of a reservoir system is disclosed that includes a flexible reservoir and an exoskeleton. The flexible reservoir is configured to expand when filled with a liquid drug. The exoskeleton is coupled to the flexible reservoir.

A system example is disclosed in which the system include a reservoir, one or more peel-able restraints positioned on the flexible reservoir. The one or more peel-able restraints are configured to seal off one or more corresponding sections of the flexible reservoir, and sequentially break to allow a liquid to fill a next corresponding section of the one or more corresponding sections of the flexible reservoir as the flexible reservoir is filled with the liquid.

DETAILED DESCRIPTION

Various systems, components, and methods related to drug delivery devices are disclosed. Each of the systems, components, and methods disclosed herein provides one or more advantages over conventional systems, components, and methods.

In order to mitigate the foregoing disadvantages of flexible reservoirs, a need therefore exists for a drug delivery device that includes a drug reservoir or reservoir that combines the advantages of fully flexible and fully rigid reservoirs while mitigating one or more disadvantages of fully flexible and fully rigid reservoirs. In addition, there is a need for a flexible reservoir system that may expand and collapse in a more predictable manner, to reduce hold up volumes and enable accurate stored fluid volume determinations, while retaining the advantages of flexible reservoirs such as high space efficiency or low pumping pressure. A further need exists for a flexible reservoir for use with a drug delivery device that has reduced holdup volume, reduced vapor transmission, and improved fill sensing capabilities.

Figure 1:
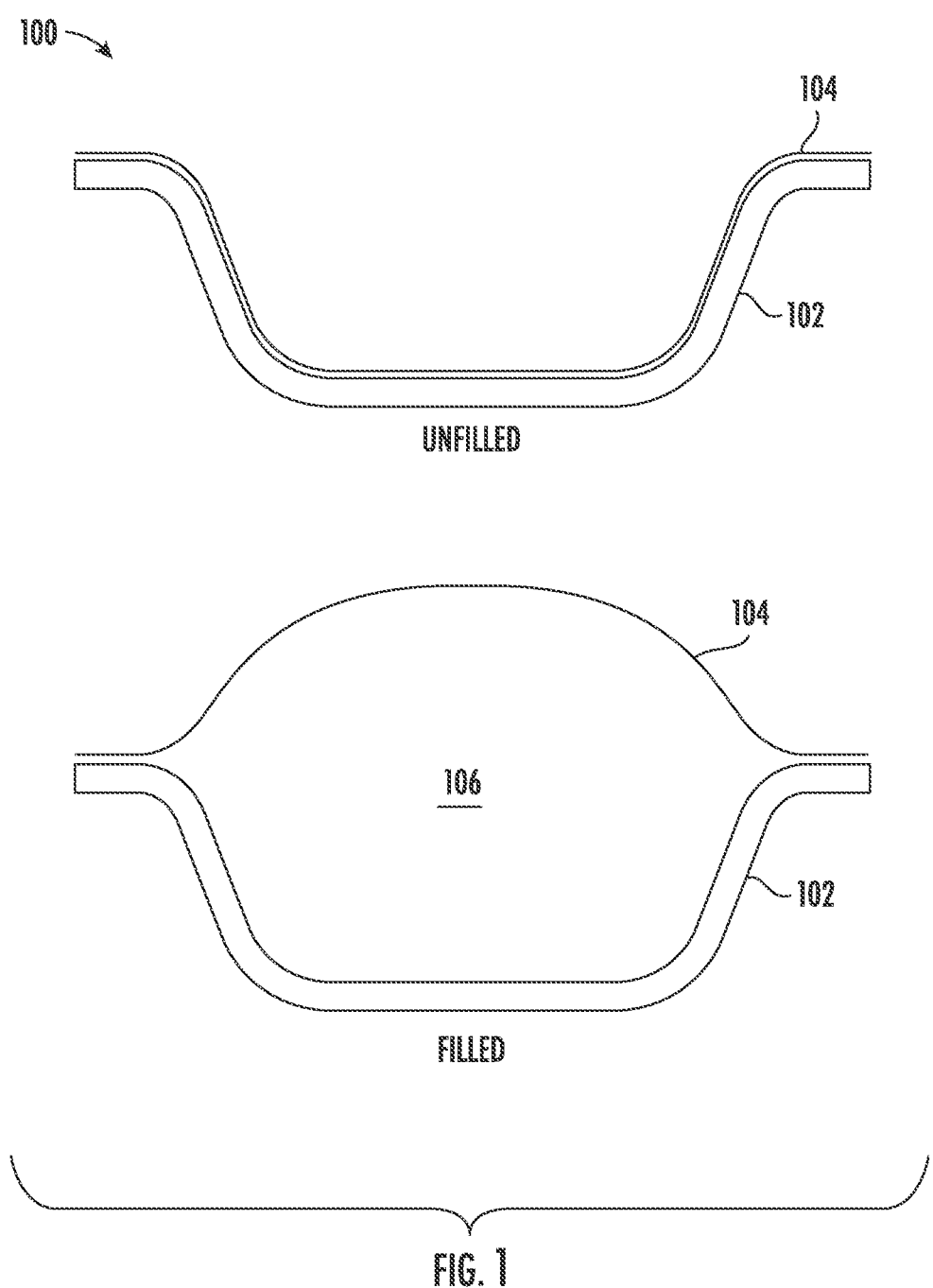
FIG. 1 illustrates a cross-sectional side view of a first example of a drug reservoir in a filled state and an unfilled state according to the disclosure.

FIG. 1 illustrates a cross-sectional side view of a first example of a drug reservoir in a filled state and an unfilled state. The combination of components for forming the reservoir (or hybrid reservoir) may, for example, allow the liquid drug to be stored and then expelled from the reservoir with relatively lower pumping pressures (as compared to fully rigid drug reservoirs) and without the need for a plunger as well as other apparent advantages.

As shown, the drug reservoir 100 includes a shell component 102 that may be rigid or semi-rigid and a flexible component 104. The shell component 102 may be formed from a variety of materials including, for example, plastic or metal, or any combination thereof. The flexible component 104 may be formed from a variety of flexible materials including, for example, a flexible plastic film. The flexible component 104 has greater flexibility than the shell component 102. FIG. 1 shows the drug reservoir 100 in an unfilled state and in a filled state. When filled, the flexible component 104 expands in response to a liquid drug (not shown) filling the drug reservoir 100 from a port (shown in other examples). The expansion of the flexible component 104 and the hermetic coupling or seal to the shell component 102 enables the drug reservoir 100 to contain a liquid drug (or other fluid or therapeutic agent) 106. The shell component 102 is an open shell. In some examples of a wearable drug delivery device, the shell component 102 may be integrated into other parts, such as a housing or chassis thereby enabling a rigid or semi-rigid shell component 102 to serve multiple purposes, such as part of a housing for the wearable drug delivery device, a structure element of another part (e.g. a battery clip or retainer) of the wearable drug delivery device, or the like.

The flexible component 104 may be coupled to the shell component 102 in a number of manners including, for example, mechanically, through use of an adhesive, or through use of an adhesive tape or the like. The coupling of the flexible component 104 to the shell component 102 is a hermetic seal thereby forming the reservoir 100 that is able to contain the liquid drug or other fluid. The shell component 102 may be of any size or shape. As shown in FIG. 1, the shell component 102 may form a bowl with an upper ridge or lip to support and provide coupling to the flexible component 104.

Figure 2:
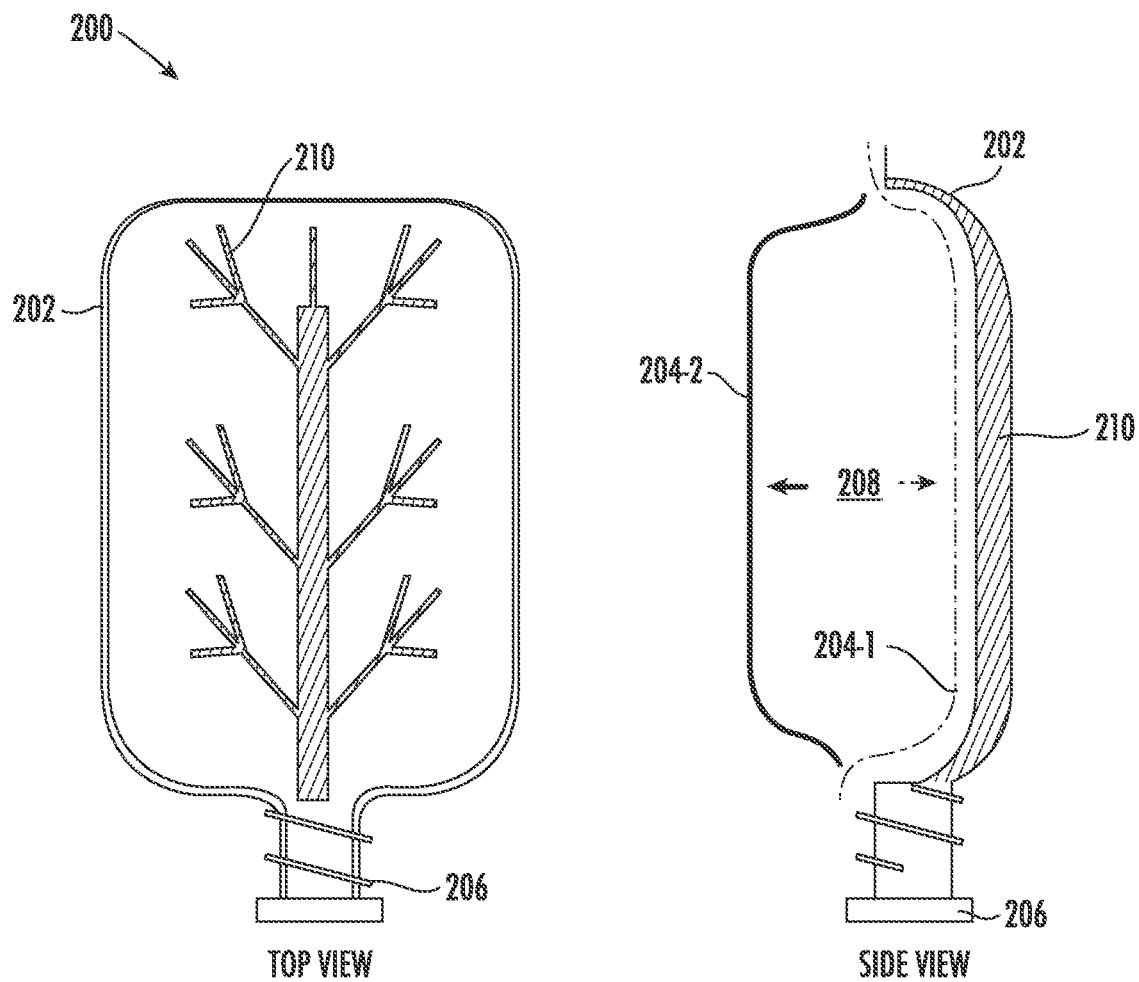
FIG. 2 illustrates a top view and a corresponding side view of a second example of a drug reservoir according to the disclosure.

FIG. 2 illustrates a top view and a corresponding side view of a second example of a drug reservoir. The drug reservoir 200 may be a particular implementation of the drug reservoir 100. The drug reservoir 200 may include a rigid or semi-rigid shell component 202 and a flexible component 204. The flexible component 204 may be formed from a thin flexible film, or the like. The shell component 202 may be an open shell. Although not shown in FIG. 2, the flexible component 204 may be sealed (i.e., coupled to form hermetic seal) to the shell component 202—for example, along a perimeter of the shell component 202. For example, an adhesive, an adhesive tape or mechanical means, such as ultrasonic welding or the like, may be used to couple or affix the flexible film component to the shell component 202. The sealing of the flexible component 204 to the shell component 202 is hermetic thereby forming the reservoir 200 that contains the liquid drug or other fluid. The side view shows the flexible component 204 in a deflated state 204-1 and in an inflated or expanded state 204-2 when filled with a fluid. When inflated or expanded, the flexible component 204 may provide a chamber 208 for storing a fluid.

The drug reservoir 200 may further include an opening or side port 206. The side port 206 may be coupled to a fluid extraction component such as, for example, a pump (not shown). The side port 206 may also be coupled to a fluid path (not shown) coupled to a patient or user of a wearable drug device containing the drug reservoir 200. The side port 206 may be formed as a portion of the shell component 202 or may be a separate component coupled to the drug reservoir 200. A liquid drug or other fluid may enter and/or exit the drug reservoir 200 from the side port 206.

As shown in the top view and the side view, the drug reservoir 200 may further include one or more recessed drainage channels 210. The drainage channels 210 may be formed into the shell component 202, for example, into an inner surface of the shell component 202. In an alternative example, the drainage channels 210, instead of being formed in the shell component 202, may be formed into the flexible component 204, for example, into an inner surface (i.e., inside the drug reservoir 200 at a surface that contacts the liquid) of the flexible component 204. In yet another alternative example, the drainage channels 210 may be formed in the shell component 202 and the flexible component 204, for example, in an inner surface of each of the shell component 202 and the flexible component 204. The drainage channels 210 may improve drainage of the drug reservoir 200, particularly as the drug reservoir 200 is nearly emptied of a stored liquid drug.

The drainage channels 210 may be formed in a number of ways to form any pattern or arrangement. In various examples, the drainage channels 210 may be formed to mimic venation patterns found on leaves. As an example, the drainage channels 210 may form a pinnate pattern or arrangement (e.g., a specific form of venation and may include a single mid-rib channel and secondary channels branching therefrom). In other examples, the drainage channels 210 may be a number of horizontal and vertical channels that are perpendicular to one another (e.g., a form of cross hatching), diagonal channels, or similar patterns of channels that facilitate drainage of the reservoir to minimize an amount of hold up volume (e.g., a volume of liquid) in the reservoir after the reservoir is drained. In addition, the channels may be a similar depth along the entire length of the channel or may have a graded depth to facilitate flow toward a port. Alternatively, or in addition, the interior of the reservoir on the film 204, the shell 202 or both may have a textured surface, such as stippling (e.g., bumps), ridges, grooves, or the like, configured to minimize the surface area upon which surfaces of film 204 and shell 202 at the interior of the reservoir 200 may contact one another as the fluid evacuates the reservoir.

Figure 3:
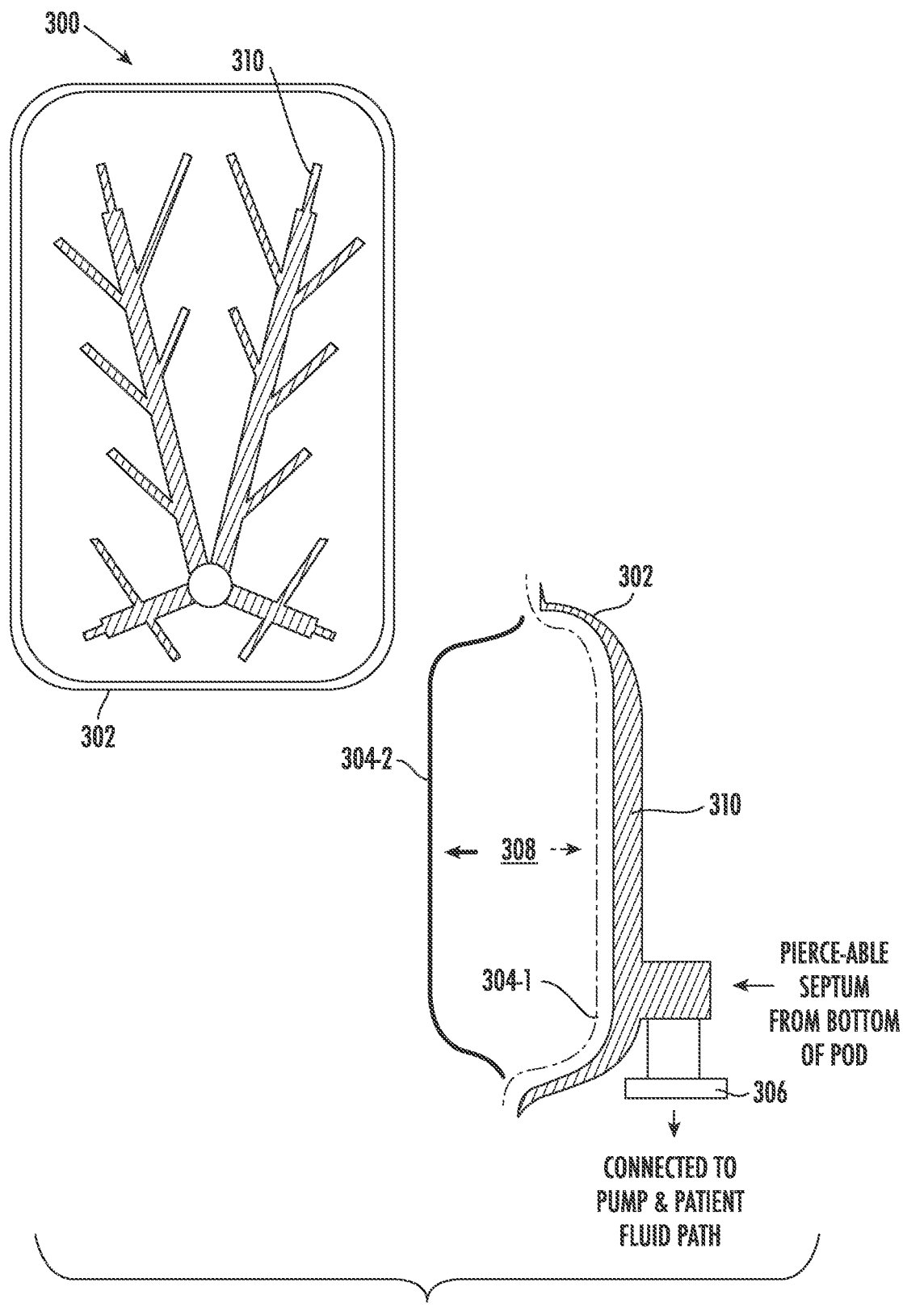
FIG. 3 illustrates a top view and a corresponding side view of a third example of a drug reservoir according to the disclosure.

FIG. 3 illustrates a top view and a corresponding side view of a third example of a drug reservoir according to the disclosure. The drug reservoir 300 may include a rigid or semi-rigid shell component 302 and a flexible film component 304. The flexible film component 304 may be sealed or coupled to the shell component 302—for example, along a perimeter of the shell component 302, to form a hermetic seal between the flexible film component 304 and the shell component 302. The corresponding side view of drug reservoir 300 shows the flexible film component 304 in a deflated state 304-1 and in an inflated or expanded state 304-2. When inflated or expanded, the flexible film component 304 may provide a chamber 308 for storing a fluid.

The drug reservoir 300 may further include an opening or central face port 306. The central face port 306 may be coupled to a fluid extraction component such as, for example, a pump. The central face port 306 may also be coupled to a fluid path coupled to a patient or user of a wearable drug device containing the drug reservoir 300. The central face port 306 may include a pierceable septum accessible from a bottom side of the drug reservoir 300. The central face port 306 may be formed as part of the shell component 302 or may be a separate component coupled to the drug reservoir 300. A liquid drug or other fluid may enter and/or exit from the central face port 306.

The drug reservoir 300 may further include one or more recessed drainage channels 310. The channels 310 may be formed into the shell component 302 (e.g., an inner surface of the shell component 302). The channels 310 may improve drainage of the drug reservoir 300, particularly as the drug reservoir 300 is nearly emptied of a stored liquid drug. For example, the circular region at the intersection of the channels 310 may be coupled to the pierce-able septum at the bottom of the pod and central face port 306 to allow the drug (not shown) to drain from the drug reservoir 300.

The channels 310 may be formed in a number of ways to form any pattern or arrangement. In various examples, the channels 310 may be formed to mimic venation patterns found on leaves. As an example, the channels 310 may form a palmate pattern or arrangement (e.g., a specific form of venation to include multiple primary channels with additional subchannels branching from a central point). In other examples, the drainage channels 210 may be a pattern of a number of horizontal and vertical channels that are perpendicular to one another (e.g., a form of cross hatching), diagonal channels, or similar patterns of channels.

Overall, the channels 210 and 310 shown may be arranged in any manner according to any design or configuration. In various examples, the channels 210 and 310 may be optimized based on the number and size of the channels 210 and 310 to reduce hold-up volume that may be present as the drug reservoirs 200 and 300 are drained.

By joining an open rigid (or semi-rigid) shell component and a flexible film sealing the open rigid shell component, the drug reservoirs disclosed herein (e.g., the drug reservoirs 100, 200, and 300) may provide a number of benefits including the following: more space efficient that a fully rigid reservoir; requires less pumping pressure than a fully rigid reservoir; and may provide more complex shapes than a fully rigid reservoir. For example, the drug reservoirs 100, 200 and 300 may be configured to have layouts that conform to occupy otherwise "dead space", or unused space, within a wearable drug delivery device. In addition, depending upon the implementation, the example drug reservoirs 100, 200 and 300 may be more robust; easier to secure; and easier to couple fluid path connections than a fully flexible reservoir. Furthermore, the intersection of the flexible film and the open rigid (or semi-rigid) shell component forms a natural hinge-like area around the open rigid shell that facilitates a controlled collapse of the flexible film into the open rigid shell component thereby allowing for a more uniform evacuation of the drug reservoir.

In various examples, the flexible film components 104, 204 and 304 disclosed herein may be coupled or sealed to the shell components 102, 202, 302, respectively, according to a number of processes including, for example: flame bonding; hot air gun; hot knife welding; hot plate welding; ultrasonic welding; an induction/impulse process; a dielectric-radio frequency process; solvent bonding, any combination thereof, or the like.

In various examples, the flexible film components 104, 204 and 304 disclosed herein may be formed to provide a tight seal with the shell components 102, 202, 302, respectively, disclosed herein to minimize any formed air gap. In various examples, the flexible film components 104, 204 and 304 may be provided by thermoforming.

Each of the drug reservoirs disclosed herein (e.g., the drug reservoirs 100, 200, and 300) may be included or used as a component of a drug delivery device including, for example, a wearable drug delivery device or an on-body drug delivery device that may store and dispense any type of drug, fluid, a therapeutic agent to a user including insulin, or the like. An example of a suitable drug delivery device in which the foregoing examples of drug reservoirs may be implemented is described in more detail with reference to the example of FIG. 9.

Figure 4:
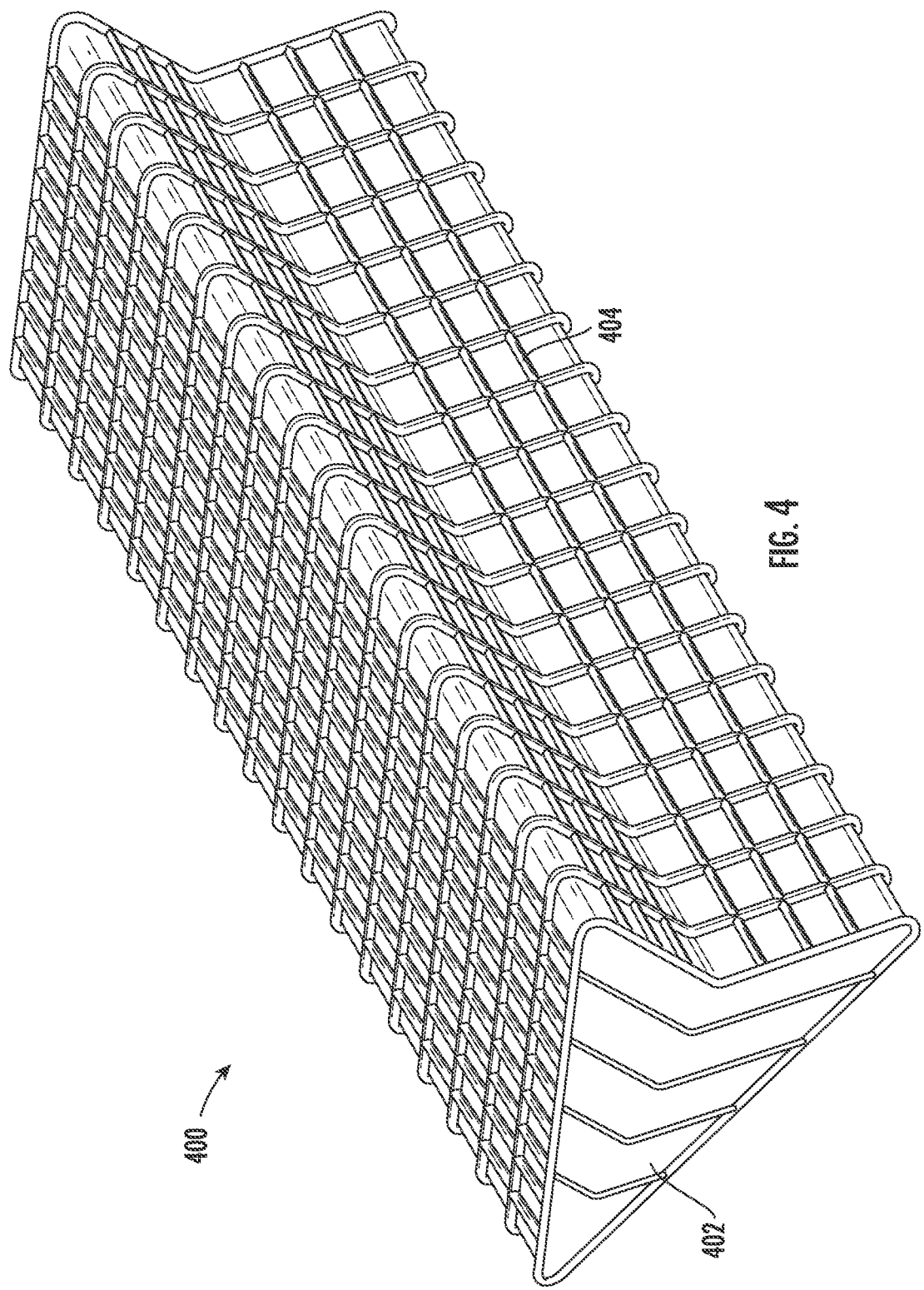
FIG. 4 illustrates an example of a flexible reservoir system.

FIG. 4 illustrates an example of a flexible reservoir system. The flexible reservoir system 400 may include a flexible reservoir 402 and an exoskeleton 404. The flexible reservoir 402 may be made of any suitable non-rigid material that allows the flexible reservoir 402 to expand when filled with a liquid or fluid and to contract or collapse when emptied or drained. The flexible reservoir 402 may be configured to hold or store any liquid or fluid such as, for example, a liquid drug or other therapeutic agent.

The flexible reservoir system 400 may be integrated into a drug delivery device or system such as, for example, a wearable or on body drug delivery device such as that described with reference to FIG. 9. The exoskeleton 404 may be formed of any suitable rigid or semi-rigid material such as, for example, metal or plastic. The exoskeleton 404 may be attached or coupled to the flexible reservoir 402 along all or a portion of the exoskeleton 404. In various examples, the exoskeleton 404 may be detached or not coupled to the flexible reservoir 402.

A rigid or semi-rigid exoskeleton 404 may surround the flexible reservoir 402 to guide the expansion and collapse of the flexible reservoir. The placement of the exoskeleton 404 creates impingement points or locations on the flexible reservoir 402 that guide the collapse or expansion as fluid leaves or is input to the flexible reservoir 402. As a result, a volume of the liquid drug stored in the flexible reservoir 402 may be more easily determined to enable accurate fill gauging. For example, hold up volume may also be reduced based on the controlled and predictable manner of collapse of the flexible reservoir 402.

FIG. 4 shows the flexible reservoir 402 in a filled or partially filled state. As shown, the flexible reservoir 402 may have a side cross-sectional shape resembling an arrowhead (or triangular) but is not so limited. In general, the flexible reservoir 402 may have any desired size and shape. The exoskeleton 404 may conform to the outer surfaces of the flexible reservoir 402 when filled and may operate or be similar to a stent. The exoskeleton 404 may have a material that has a higher elastic modulus than the material that forms the flexible reservoir 402. As further shown in FIG. 4, the exoskeleton 404 may form a cross-hatching or lattice arrangement (or cage) around the flexible reservoir 402. In an unfilled or compressed state, the flexible reservoir 402 may lay substantially flat along with the exoskeleton 104 also being able to fold over, collapse, and/or lay substantially flat on top of and/or around the flexible reservoir 402.

The flexible reservoir system 400—by including the exoskeleton 404—may improve control of the expansion and the collapse of the flexible reservoir 402 during filling and emptying of the flexible reservoir, respectively. The rigid and/or semi-shell components of the exoskeleton 404 may aid or guide the change of shape of the flexible reservoir 402 such that as it expands or collapses, it does so in a predictable and expected manner. By guiding the expansion and collapse of the flexible reservoir 402, the exoskeleton 404 may improve operation of the flexible reservoir system 400.

In particular, the exoskeleton 404 may improve fill gauge sensing in relation to the flexible reservoir system 400 as the exoskeleton 404 may ensure that the displacement of the flexible reservoir 402 as it is filled or emptied involves known displacement or movement, allowing the volume of the flexible reservoir to be determined more easily.

Additionally, the exoskeleton 404 may reduce hold up volume associated with the flexible reservoir 402 as the controlled collapse of the flexible reservoir 402 provided by the exoskeleton 404 is more predictable and consistent for each collapse.

Figure 5:
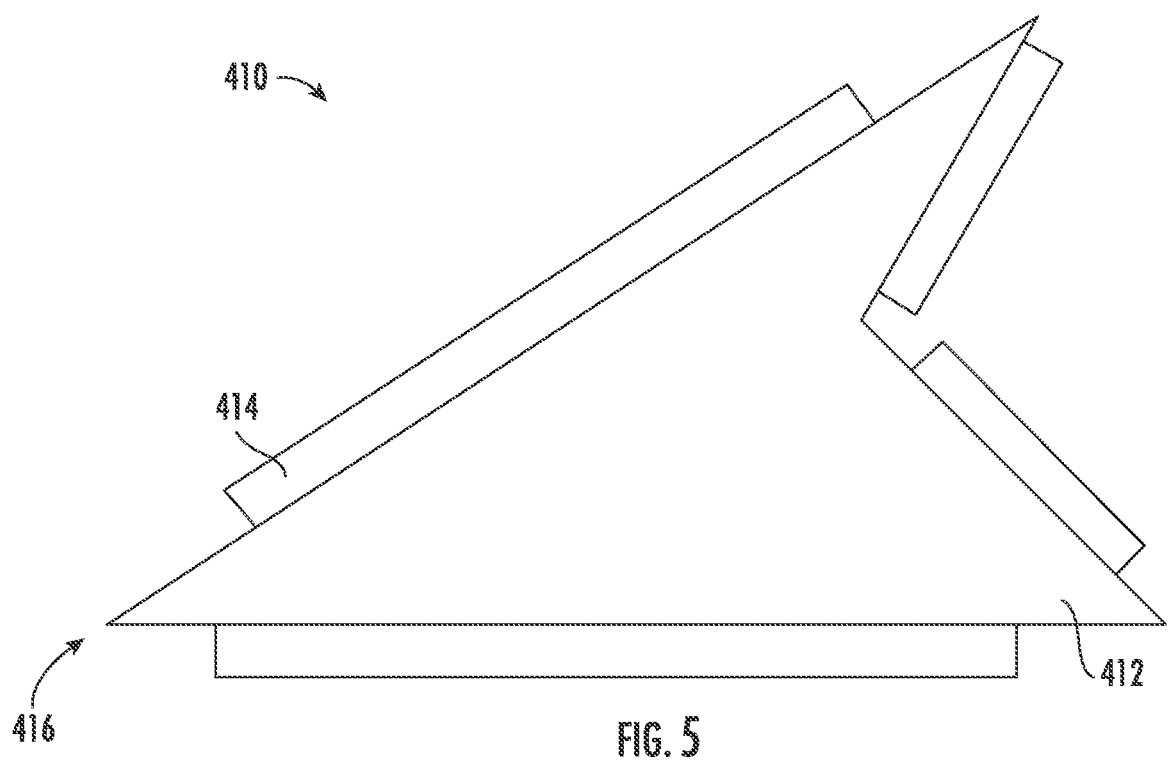
FIG. 5 illustrates another example of a flexible reservoir system.

FIG. 5 illustrates another example of a flexible reservoir system. The flexible reservoir system 410 may include a flexible reservoir 412 and rigid panels 414. The flexible reservoir 412 may be made of any suitable non-rigid material that allows the flexible reservoir 412 to expand when filled with a liquid or fluid and to contract or collapse when emptied or drained. The flexible reservoir 412 may be configured to hold or store any liquid or fluid such as, for example, a liquid drug or other therapeutic agent.

The flexible reservoir system 410 may integrated into a drug delivery device or system such as, for example, a wearable or on body drug delivery device. The flexible reservoir system 410 may include one or more rigid panels 414, with each rigid panel 414 attached a flat surface of the flexible reservoir 412 as shown. The rigid panels 414 may add structure to the flexible reservoir. As shown in FIG. 5, hinge points 416 may be positioned at angled portions or crease portions (or vertices of the different angles) of the flexible reservoir 412. The hinge points 416 may be introduced or created by attachment of the rigid panels 414 to the flexible reservoir 412, or by use of the exoskeleton 404 of FIG. 4.

The flexible reservoir 412 shown in FIG. 5 is in a filled or partially filled state (e.g., a side view of the flexible reservoir 412). As shown, the flexible reservoir 412 may have a side cross-sectional shape resembling an arrowhead (or triangular) but is not so limited. In general, the flexible reservoir 412 may have any desired size and shape. The attachment and positioning of the rigid panels 414 to the flexible reservoir 412 may help determine the shape of the flexible reservoir 412 and may guide the expansion and collapse of the flexible reservoir 412 as it is filled or drained. In various examples, the rigid panels 414 may rotate about the hinge points 416 or rotate relative to one another as the flexible reservoir 412 is filled or emptied.

In various examples, the flexible reservoir 412 may be substantially the same as the flexible reservoir 402. The placement of the rigid panels 414 may accommodate and guide movement of the flexible reservoir 412 in a controlled and predictable manner. The rigid panels 414 may be formed of any suitable material including, for example, metal or plastic. In general, the rigid panels 414 may be formed to be relatively thin in relation to a size of the flexible reservoir 412. The rigid panels 414 may be attached to the flexible reservoir 412 by any suitable means.

The rigid panels 414 may facilitate volume determination of a fluid occupying the flexible reservoir 412. For example, angles of the flexible reservoir 412, angles of the created hinge points 416, and/or movement or displacement of the rigid panels 204 (e.g., relative to one another or to a fixed reference point) may be used to estimate an amount of fluid contained within the flexible reservoir 412 as each of these components and features of the flexible reservoir system 410 change upon expansion and collapse. As with the flexible reservoir system 400, the flexible reservoir system 410 may reduce hold up volume as the rigid panels provide controlled collapse of the flexible reservoir 412 during the evacuation of fluid from the flexible reservoir 410, resulting in a more predictable and consistent collapse of the flexible reservoir 410. The examples in FIGS. 4 and 5 provide a reservoir system that fills and empties in a predictable manner due to the use of the exoskeleton. The predictability enables sensors to be used to provide reliable volume sensing (e.g., a fill gauge) so measurements of how much liquid drug remains, has been dispensed and other information related to the volume of the liquid drug, the reservoir or the operation of the wearable device may be provided to a user. The materials of the exoskeleton and the flexible reservoir may be the same, or different. To achieve the structural features that enable the predictable collapse or fill of the reservoir, different thicknesses of the same material and/or different materials having a different modulus of elasticity from one another may be used to form the illustrated examples.

Figure 6:
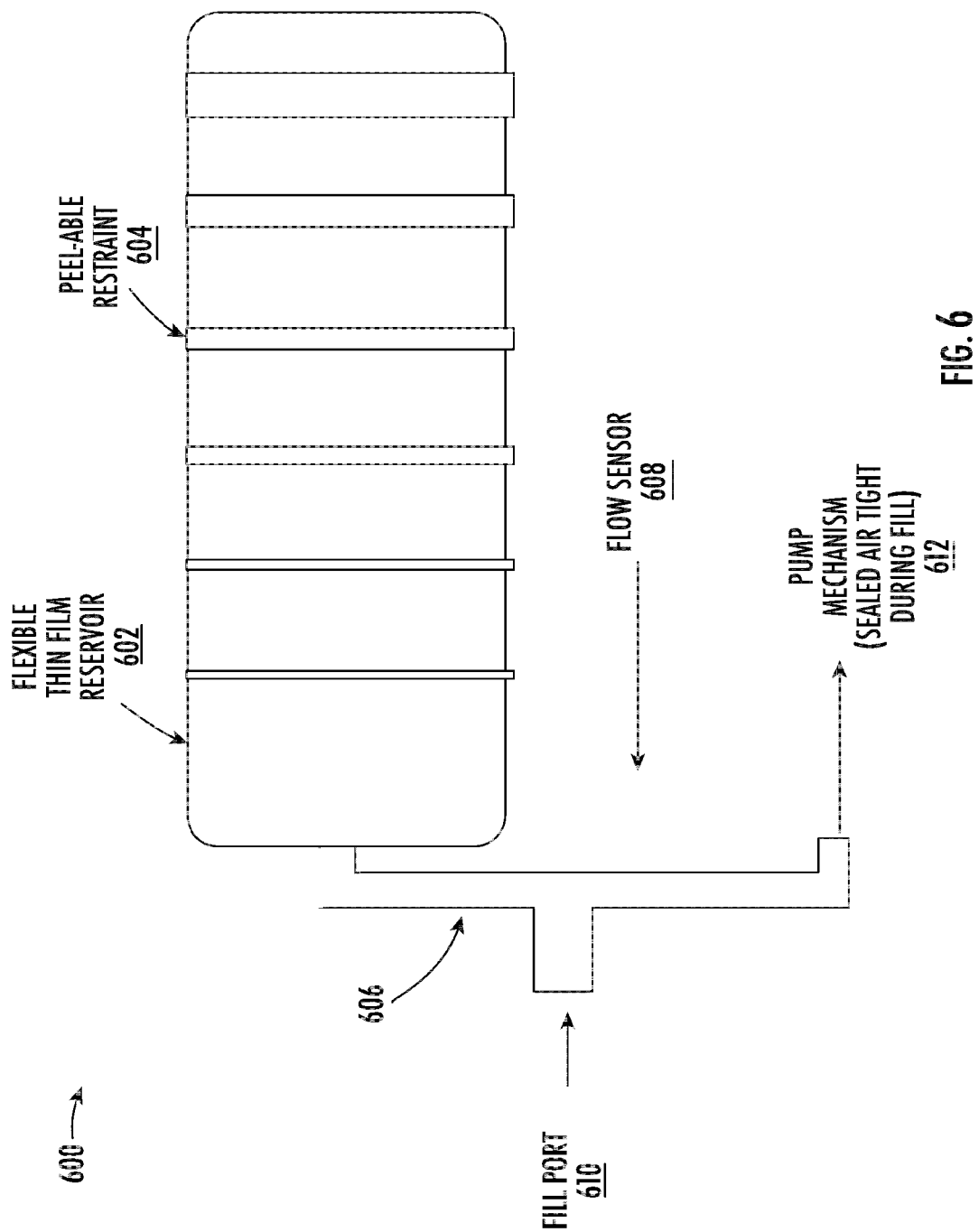
FIG. 6 illustrates a subsequent example of a reservoir.
Figure 7:
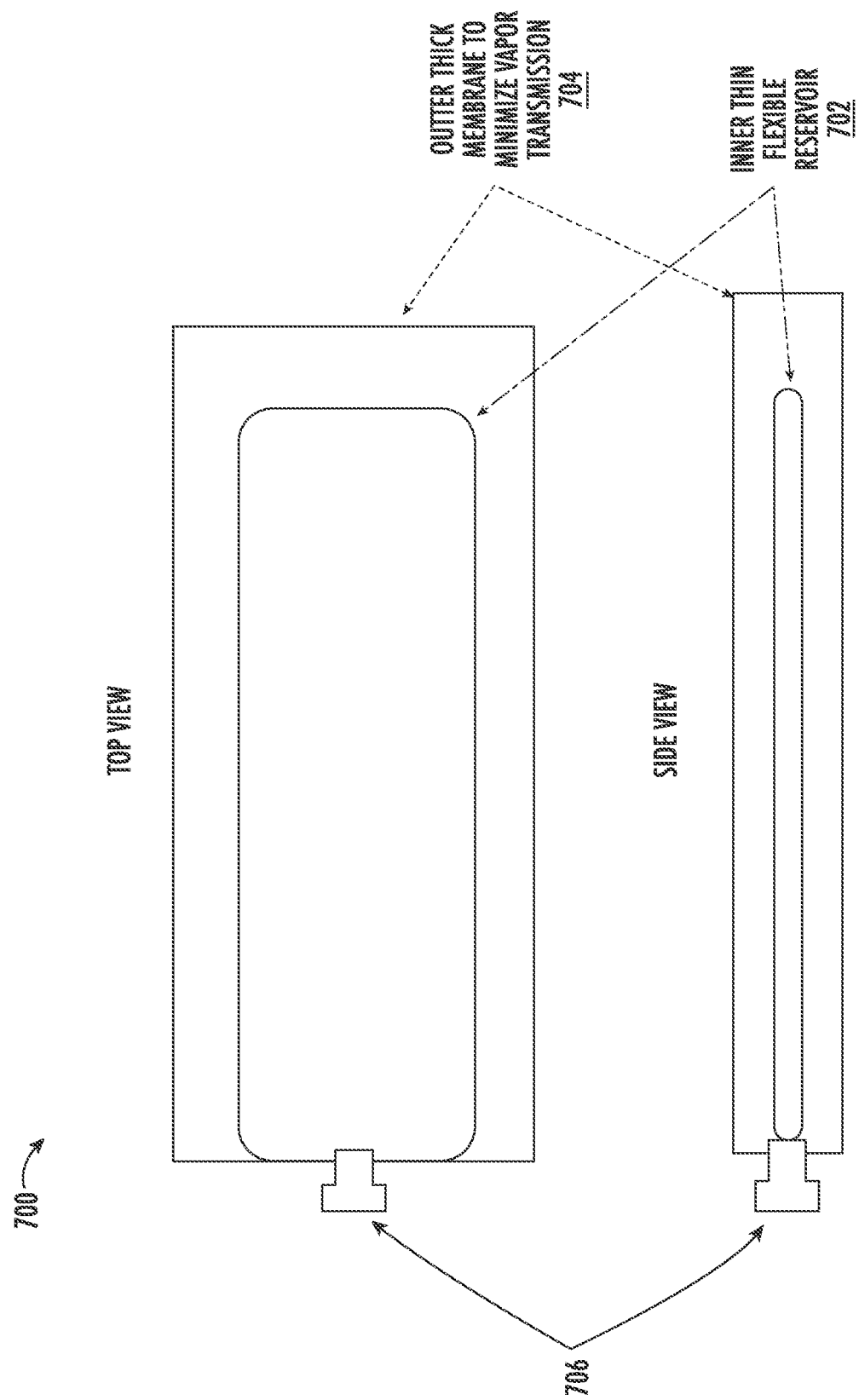
FIG. 7 illustrates an additional example of a reservoir.
Figure 8:
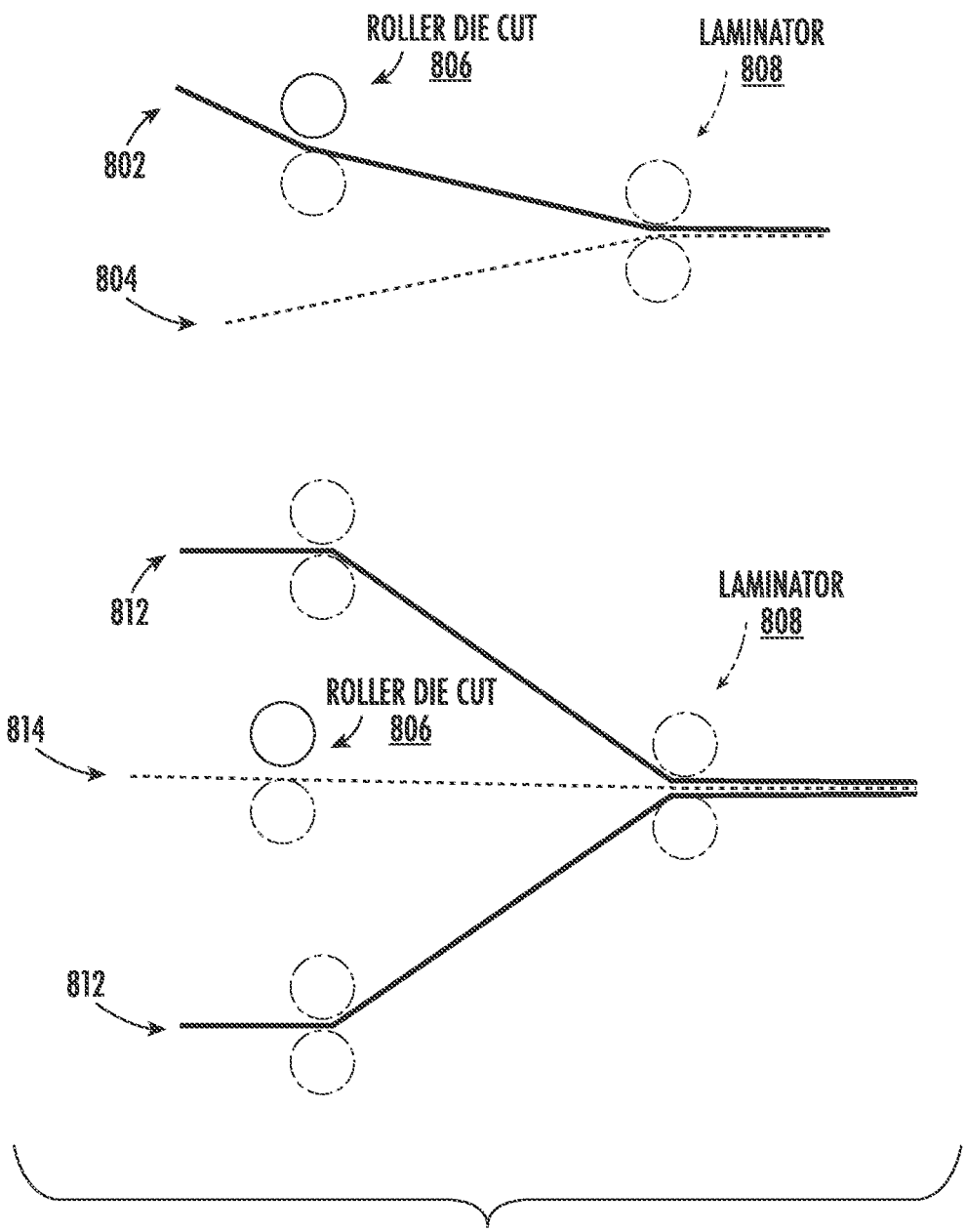
FIG. 8 illustrates examples of processes for forming a multilayer reservoir.

In the various examples of FIGS. 6-8 of another reservoir system, the reservoir systems in a wearable drug delivery system, for example, may also be configured to store a liquid drug.

FIG. 6 illustrates a first example of a reservoir. As shown in FIG. 6, the reservoir 600 may include a reservoir 602 and peel-able restraints (or dividers) 604. The reservoir 600 may couple to a fluid path component 606 that includes a flow sensor 608 and to a pumping mechanism 612 (not shown but described in more detail with reference to another example). The reservoir 602 may be a flexible thin film reservoir. The peel-able restraints 604 may be peel-able heat stakes or the like. For example, the peel-able restraints 604 may be held together with a weak adhesive having known holding properties or the like. The fluid path component 606 may be coupled to the reservoir 602. The fluid path component 606 may include a fill port 610 and may also be coupled to a pumping mechanism 612. As shown in another example, the flow sensor 608 may be positioned between the fill port 610 and the pumping mechanism 612. The reservoir 600 may be part of a drug delivery device or system such as, for example, a wearable drug delivery device or system.

In various examples, the fill port 610 may provide access to a fluid such as, for example, a liquid drug. The pumping mechanism 612 (details not shown in FIG. 6 for simplicity) may be any type of pumping mechanism or system for extracting fluid from the reservoir 602. The pumping mechanism 612 may be operated to provide stored fluid within the reservoir to, for example, a user or patient using the wearable drug delivery device of which the reservoir system 600 is a part.

In various examples, a first process may be used to form the reservoir 602 and a second or supplemental process may be used to form and position the peel-able restraints 604. The peel-able restraints 604 may form zones within the reservoir 602. The peel-able restraints 604 may seal or block off portions or sections of the reservoir 602 that may remain sealed until broken during a filling process. For example, the peel-able restraints 604 may seal off corresponding sections of the reservoir 602 and may be released or opened as more fluid enters the reservoir 602 during a filling process. A pressure/force from the fluid/filling process may cause the peel-able restraints 604 to open or break sequentially, thereby providing access to another corresponding sealed off section of the reservoir 602. In this manner, a filling process of the reservoir 602 may be closely controlled—for example, to ensure that corresponding sections or zones determined by the peel-able restraints 604 are sequentially filled. In an operational example, one or more peel-able restraints 604 may be positioned on the reservoir 602 to seal off one or more corresponding sections (i.e., areas between respective peel-able restraints) of the reservoir 602. In an example, each corresponding section of the one or more corresponding sections is completely filled with the liquid drug before a next section is opened for filling by breaking a next corresponding peel-able restraint. An initial section (e.g., the section of the reservoir 602 closest to the fluid path component 606) of the reservoir 602 may be filled, eventually a first peel-able restraint (closest to the fluid path component 606) of the peel-able restraints 604 may sequentially break, enabling the liquid drug to sequentially fill the corresponding section of the reservoir 602. In this way, the reservoir 602 is filled in a predictable and controlled manner—with each section formed by the peel-able restraints filled one after another.

In various examples, the filling process may open any number of the peel-able restraints 604 but is not limited to opening all of the peel-able restraints 604. That is, only a portion of the reservoir 602 may be filled such that some peel-able restraints 604 remain closed, thereby allowing certain corresponding sections of the reservoir 602 to remain sealed off. In general, the arrangement of the peel-able restraints 604 may guide the filling process of the reservoir 602 in a predictable and/or controlled manner.

As shown in FIG. 6, the peel-able restraints 604 may have increasing widths (e.g., moving from an end of the reservoir 602 coupled to the fluid path component 606 to an end of the reservoir 602 not coupled to the fluid path component 606). The increasing widths of the peel-able restraints 604 may provide increasing strengths for the peel-able restraints 604, such that the peel-able restraints 604 having larger widths require more force to open than peel-able restraints 604 having smaller widths. This allows for tuning of the filling of the reservoir 602. The arrangement and increasing widths of the peel-able restraints 604 as shown in FIG. 6 may ensure that the peel-able restraints 604 open sequentially in a controlled manner—for example, one at a time to provide the fluid to a current corresponding section to first fill completely before opening a next peel-able restraint 604. In an example, increased pressure needed to break into the next corresponding section may provide a pressure "signature" that may be used for fill sensing. For example, the peel-able restraint between a first corresponding section and a second corresponding section may break at 2 pounds per square inch (psi), while the peel-able restraint between the second corresponding section and a third corresponding section may break at 4 psi, so on until the reservoir is filled to a desired volume. Alternatively, the respective pressure "signature" for each corresponding section may be the same (e.g. 2.5 psi). A fill sensing module, which may be a logic circuit or the like coupled to the flow sensor or pressure sensor (e.g., pressure gauge or the like), may detect pressure spikes and pressure drops to infer that a peel-able restraint broke and the liquid drug is flowing into a next corresponding section. Of course, other methods such as detecting changes in resistance or capacitance may also be used to provide fill sensing with use of a logic circuit.

The reservoir 602 may have any shape and/or form factor. The peel-able restraints 604 may also have any shape and may be arranged in any desired manner onto the reservoir 602. In an example, the reservoir 602 may be circular and the peel-able restraints 604 may be formed in concentric circles on the reservoir 602. In an example, the peel-able restraints 604 may be formed along a gradient (e.g., with increasing or decreasing sized corresponding sections).

The reservoir system 600 may provide several advantages. For example, by establishing separate fillable sections or zones within the reservoir, holdup volume, reservoir air volume, and vapor transmissivity may be reduced.

In some instances, the flexible films that form the reservoirs have vapor transmissivity that permits water vapor to pass through the flexible film after time. The exposure to water vapor over time can reduce the potency of a drug stored in the reservoir. As a further advantage of the reservoir 602 related to vapor transmissivity, at lower fill volumes, fewer compartments or sections formed by the peel-able restraints 604 may be filled by the fluid or drug. As a result, the interior surface area of the reservoir 602 that contacts the fluid may be reduced (e.g., in comparison to a flexible reservoir not having peel-able restraints 604). By reducing the interior surface area of the reservoir 602 in contact with the fluid, the rate of vapor transmission to the stored fluid may be reduced (e.g., since the ratio of the surface area of the interior of the reservoir to the fill volume). For example, the reservoir 602 is to be filled with a volume of drug that is one-tenth of the capacity of the entire reservoir. Since reservoir 602 has the peel-able restraints 604, by filling a first section or sections equal to the volume of drug, the exposure of the drug to an interior surface area of the reservoir remains at a consistent ratio of fill volume to surface area to which the drug is exposed. For example, a reservoir, such as 602, may have an interior surface area of 100 square millimeters and assume a volume of drug equaling one-tenth of the fill capacity (i.e., volume of drug that the reservoir is capable of holding) of the reservoir is input into the reservoir. By using a reservoir 602 having the peel-able restraints 604, the amount of the drug that is exposed to an interior surface of the reservoir may be limited to, for example, one-tenth of the interior surface area of the reservoir. By maintaining a consistent ratio of exposed interior surface area to liquid drug volume, the potency of the drug may be prolonged due to the reduced exposure to water vapor. The consistent ratio may be based on the particular drug and the material of the flexible film. In other examples, the solution of the liquid drug may pass through the reservoir 602 thereby leaving less liquid volume in the reservoir 602. In addition, other proteins from the liquid drug may be left behind, which affects drug concentration and potency.

Furthermore, hold up volume may be reduced at lower fill volumes. The peel-able restraints 604 will also maintain a near vacuum state inside the reservoir 602 during storage, preventing trapped air from affecting performance of the reservoir system 600.

The reservoir system 600 also may provide accurate fill sensing based on detected changes in pressure or flow rate when the peel-able restraints 604 break at known positions. For example, the arrangement of the peel-able restraints 604 may cause pressure pulses (e.g., when the dividers are broken) that may correspond to different fill volumes that may be detected by the flow sensor 608. The detected flow volume may reflect the changes in pressure related to the fill volume. Alternatively, a pressure sensor could also be used in a similar location as the flow sensor 608 to estimate fill volume—for example, by detecting a pressure drop after each restraint (e.g., a peel-able restraint 604) "breaks." In general, the sensor 608 may detect changes in pressure and/or flow that may be related to fill volume of the reservoir 602 based on the known positions of the peel-able restraints 604 (and/or the known sizes of the different compartments formed by the peel-able restraints 604). Other sensors could also be alternatively used to detect fill volume.

Often, the desire for a thin and flexible reservoir may make it challenging to make the reservoir less susceptible or prone to vapor transmission. FIG. 7 illustrates a subsequent exemplary reservoir system 700. The reservoir system 700 provides a solution to these somewhat competing goals or requirements for a reservoir by using the thin film reservoir 702 and a separate membrane 704 as a vapor barrier. As shown in FIG. 7, the reservoir system 700 includes a reservoir 702 and an outer membrane 704. The reservoir 702 may be a flexible thin film reservoir. In an example, in configurations where an amount of free space or air volume is to be limited at maximum fill of the reservoir system 700, the outer membrane 704 may be part of or integrated into the housing of wearable drug delivery device (not shown in this example). In another example, the outer membrane 704 may surround the inner thin film reservoir 702. The inner thin film reservoir 702 may include a port or opening 706. The outer membrane 704 may be a relatively thick membrane (e.g., in comparison to the thickness of the reservoir 702)

and/or have improved water vapor transmissivity than the inner thin film reservoir 702. The outer membrane 704 may be configured to reduce or minimize vapor transmission. A top view and a corresponding side view of the reservoir system 700 are both shown in FIG. 7.

By doing so, each component may be separately optimized to meet overall design requirements. In various examples, the reservoir 702 and the membrane 704 may be made of the same material (e.g., with different thicknesses). In various examples, the reservoir 702 and the membrane 704 may be made of different materials. In some examples, the reservoir 702 and the membrane 704 may not be laminated together, but in other example, the reservoir 702 and the membrane 704 may be laminated together.

FIG. 8 illustrates exemplary processes for forming a multilayer reservoir. The processes may be used to form the reservoirs 602 or 202. In the top figure, a first membrane material 802 may be die cut by a cutter 806. The first membrane material 802 may then be laminated to a second membrane material 804 by a laminator 808. For example, the second material 804 may be configured to function as a localized stiffener. In an example, the first membrane material 802 may be a thin film that is easy to bend. In an example, the second membrane material 804 may provide a good vapor barrier and may be stiffer than the first membrane material 802. Alternatively, in the top figure, the first membrane material 802 or the second membrane material 804 may be configured to contact the drug and be utilized as an interior surface of a reservoir.

The process shown in the top figure of FIG. 8 provides a technique for joining materials with different benefits to form a multilayer reservoir with localized stiffener. In an example, the second membrane material 804 may be polychlorotrifluoroethylene (PCTFE) (also referred to by the brand name Aclar®) or the like. The laminated result shown in the top process may provide localized areas that facilitate easier folding, manufacturing, and consistent collapse of a flexible reservoir, while maintaining desired vapor barrier properties across most of the surface area as a result of the lamination.

In the bottom figure of FIG. 8, the top and bottom materials 812 may be of the same material as the first membrane material 802 in the top figure of FIG. 8 or the materials 812 may be a different. The middle material 814 may be a different material than the membrane material 804. The material 812 on the top and bottom may be laminated together through die cut holes (e.g., formed by cutter 806) formed in the middle material 814. Again, in an example, the middle material 814 may provide enhanced vapor barrier properties. The process shown in this bottom figure of FIG. 8 may allow the formation of a multilayer reservoir using dissimilar materials that may be hard to laminate together—accordingly, holes in the middle layer material are formed such that lamination of the materials 812 to one another may form the multilayer reservoir by coupling the outer similar material 812 layers together. Such an arrangement may be beneficial because it provides both the flexibility required for a collapsible reservoir as well as the vapor barrier properties desired to mitigate against loss of potency of any liquid drug within the reservoir.

Examples of materials suitable for use in producing the respective flexible films of the examples shown in FIGS. 1-8 include low-density polyethylene, polypropylene, polypropylene/PCTFE laminate, PCTFE, Aclar CP or the like.

Figure 9:
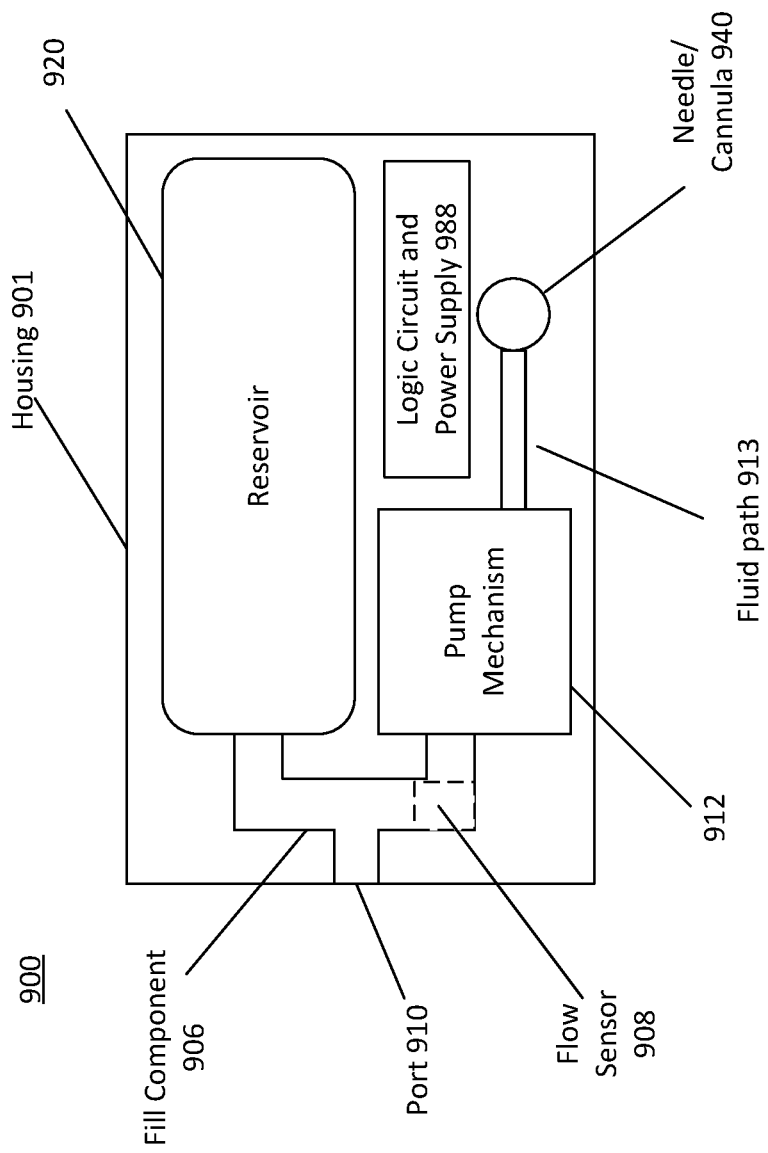
FIG. 9 illustrates an example of a wearable drug delivery device suitable for use with the reservoir examples of FIGS. 1-7.

FIG. 9 illustrates an example of a wearable drug delivery device suitable for use with the reservoir examples of FIGS. 1-7. As shown in FIG. 9, the wearable drug delivery device 900 includes housing 901, a reservoir 920, a fluid path component 906, and a pump 912. Although not shown, the wearable drug delivery device 900 may be attached to a user via an adhesive tape or the like. The housing 901 may also be a chassis for the wearable drug delivery device. The reservoir 920 may be a flexible thin film reservoir (as shown in the examples of FIGS. 6-8), a shell/flexible film hybrid reservoir (such as the examples shown in FIGS. 1-3), a flexible reservoir with exoskeleton (as shown in the examples of FIGS. 4 and 5), or the like. In examples in which the reservoir 920 includes a shell component, such as 102, 202 and 302 of FIGS. 1-3, the shell component may be integrated into other parts of the wearable drug delivery device, such as the housing 901, thereby enabling the rigid or semi-rigid shell component of the reservoir 920 to serve multiple purposes, such as a backside of a housing for the wearable drug delivery device 900, or the like.

The fluid path component 906 may be coupled to the reservoir 920. The fluid path component 906 may include a fill port 910 and may also be coupled to a pumping mechanism 912. A flow sensor 908 suitable for use in determining a volume of drug delivered may be positioned within the fluid path component 906 between the fill port 910 and the pumping mechanism 912. Alternatively, a flow sensor 908 may be near the entrance of the reservoir 920 so a drug volume input to the reservoir 920 may be determined.

In an example, the reservoir system of FIG. 6 may be used and may include a fluid path component 906 of the wearable drug delivery device 900 coupled to the reservoir 920 and a pumping mechanism, with the pumping mechanism configured to extract a fluid contained in the reservoir. In the example utilizing the reservoir system of FIG. 6, a flow sensor 908 may be coupled between a fill port of the fluid path and the pumping mechanism and may detect a fill volume of the reservoir based on pressure changes or flow changes as the peel-able restraints sequentially break. Further, the breaking of peel-able restraints positioned at known locations may provide for fill sensing.

In addition, or in another example, a vapor barrier membrane, such as 704 in the example of FIG. 7, may be positioned around the reservoir 920 to reduce vapor transmission.

In various examples, the fill port 910 may provide access to a fluid such as, for example, a liquid drug. The pumping mechanism 912 may be any type of pumping mechanism or system for extracting fluid from the reservoir 920. Examples of pump mechanisms suitable for use as pump mechanism 912 may be found in U.S. patent application Ser. No. 16/433,481 filed on Jun. 6, 2019 and Ser. No. 16/054,323 filed on Aug. 3, 2018, the entire contents of each application incorporated herein by reference. Of course, other pump mechanisms may be used. The pump mechanism 912 may be coupled to a fluid path 913 and a needle or cannula 940. The needle or cannula 940 may be configured to complete a fluid pathway from the fluid path 913 to a user by fluidly coupling to the fluid path 913 and penetrating the skin of the user (not shown). The pumping mechanism 912 may be operated to provide fluid stored within the reservoir 920 for example, via the fluid path 913 and needle/cannula 940 to a user or patient wearing the wearable drug delivery device 900. An example of a system for delivering drugs is provided in U.S. patent application Ser. No. 15/359,187, filed Nov. 22, 2016, which is herein incorporated by reference in its entirety.

The wearable drug delivery device 900 may also include a logic circuit and a power supply 988. The logic circuit may be coupled to the pump mechanism 912, the flow sensor 908 and optionally other components, such as the peel-able constraints, when the reservoir example of FIG. 6 is utilized. An example of a suitable power supply may be batteries, or the like. The logic circuit and power supply 988 may include a memory (not shown) for storing programming code and information. The logic circuit and power supply 988 may be configured to control and receive inputs from the pump mechanism 912, the flow sensor 908 and other components, such as the peel-able constraints, if present. In addition, the logic circuit and power supply 988 may be configured to and perform calculations and processes based on inputs received from inputs from the pump mechanism 912, the flow sensor 908, and other components, such as the peel-able constraints, or the like.

Certain examples of the present invention were described above. It is, however, expressly noted that the present invention is not limited to those examples, but rather the intention is that additions and modifications to what was expressly described herein are also included within the scope of the invention. Moreover, it is to be understood that the features of the various examples described herein were not mutually exclusive and may exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

The invention claimed is:

1. A wearable drug delivery device, comprising:
    a reservoir for storing a liquid drug, comprising:
        a shell component extending in at least one dimension of the reservoir;
        a flexible component coupled to the shell component, wherein the coupling is a hermetic seal around a perimeter of the flexible component; and
        a port operable to fill and empty the reservoir, wherein the port includes:
            a pierce-able septum accessible at a bottom surface of the wearable drug delivery device; and
            a central face in a side of the shell component that is in fluid communication with a fluid path to a user of the wearable drug delivery device,
            wherein the pierce-able septum is perpendicular to the central face; and
            a port opening fluidly coupled to a plurality of drainage channels disposed along an inner surface of the shell component,
            wherein the shell component is semi-rigid, configured to store a portion of the liquid drug, and the plurality of drainage channels are configured to direct the liquid drug across the inner surface into the port opening during emptying of the reservoir.

2. The wearable drug delivery device of claim 1, wherein the shell component is integrated in a chassis of the wearable drug delivery device.

3. The wearable drug delivery device of claim 1, wherein the shell component comprises an open shell.

4. The wearable drug delivery device of claim 1, wherein the flexible component is operable to:
    expand as the reservoir is filled with a liquid, and
    collapse as the reservoir is emptied of the liquid.

5. The wearable drug delivery device of claim 1, wherein the port is coupled to the shell component.

6. The wearable drug delivery device of claim 1, wherein the plurality of drainage channels directly contact the liquid drug when the liquid drug is stored in the reservoir.

7. The wearable drug delivery device of claim 1, wherein the shell component of the reservoir is positioned against an interior of the bottom surface of the wearable drug delivery device.

8. A wearable drug delivery device, comprising:
    a reservoir for storing a liquid drug, comprising:
        a shell component;
        a flexible component coupled to the shell component, wherein the coupling is a hermetic seal and one or more drainage channels formed into the flexible component; and
        a port operable to fill and empty the reservoir, wherein the port includes:
            a pierce-able septum accessible at a bottom surface of the wearable drug delivery device; and
            a central face in a side of the shell component that is in fluid communication with a fluid path to a user of the wearable drug delivery device, wherein the pierce-able septum is perpendicular to the central face.

9. The wearable drug delivery device of claim 8, wherein the shell component is integrated in a chassis of the wearable drug delivery device.

10. The wearable drug delivery device of claim 8, wherein the shell component comprises an open shell and is rigid or semi-rigid.

11. The wearable drug delivery device of claim 8, wherein the flexible component is operable to:
    expand as the reservoir is filled with a liquid, and
    collapse as the reservoir is emptied of the liquid.

12. The wearable drug delivery device of claim 8, wherein the port is coupled to the shell component.

13. The wearable drug delivery device of claim 8, wherein the reservoir further comprises:
    one or more drainage channels formed in the shell component that directly contact the liquid drug when the liquid drug is stored in the reservoir.

14. The wearable drug delivery device of claim 8, wherein the shell component of the reservoir is positioned against an interior of the bottom surface of the wearable drug delivery device.

15. A wearable drug delivery device, comprising:
    a reservoir for storing a liquid drug, comprising:
        a shell component;
        a flexible component coupled to the shell component, wherein the coupling is a hermetic seal and one or more drainage channels are formed into both the shell component and the flexible component; and
        a port operable to fill and empty the reservoir, wherein the port includes:
    a pierce-able septum accessible at a bottom surface of the wearable drug delivery device; and
        a central face in a side of the shell component that is in fluid communication with a fluid path to a user of the wearable drug delivery device, wherein the pierce-able septum is perpendicular to the central face.

16. The wearable drug delivery device of claim 15, wherein the shell component is integrated in a chassis of the wearable drug delivery device.

17. The wearable drug delivery device of claim 15, wherein the shell component comprises an open shell and is rigid or semi-rigid.

18. The wearable drug delivery device of claim 15, wherein the flexible component is operable to:
   expand as the reservoir is filled with a liquid, and
   collapse as the reservoir is emptied of the liquid.

19. The wearable drug delivery device of claim 15, wherein the port is coupled to the shell component.

20. The wearable drug delivery device of claim 15, wherein the shell component of the reservoir is positioned against an interior of the bottom surface of the wearable drug delivery device.

* * * * *